US006660054B2

(12) United States Patent
Manna et al.

(10) Patent No.: US 6,660,054 B2
(45) Date of Patent: Dec. 9, 2003

(54) FINGERPRINT PROCESSING CHAMBER WITH AIRBORNE CONTAMINANT CONTAINMENT AND ADSORPTION

(75) Inventors: Ronald R. Manna, Valley Stream, NY (US); Dan Voic, Clifton, NJ (US); Scott Isola, Deer Park, NY (US); Michael Pinka, Bayshore, NY (US)

(73) Assignee: Misonix, Incorporated, Farmingdale, NY (US)

( * ) Notice: Subject to any disclaimer, the term of this patent is extended or adjusted under 35 U.S.C. 154(b) by 0 days.

(21) Appl. No.: 09/950,333

(22) Filed: Sep. 10, 2001

(65) Prior Publication Data

US 2002/0124537 A1 Sep. 12, 2002

Related U.S. Application Data

(60) Provisional application No. 60/231,638, filed on Sep. 11, 2000.

(51) Int. Cl.⁷ .............................. A61B 5/117; F23J 11/00
(52) U.S. Cl. .................... 55/385.2; 55/DIG. 18; 454/187; 427/1; 427/145; 106/31.03; 106/31.15; 118/31.5; 252/374
(58) Field of Search .................. 55/385.2, DIG. 18; 454/187; 427/1, 145; 106/31.03, 31.15; 118/31.5; 252/374

(56) References Cited

U.S. PATENT DOCUMENTS

| | | | | |
|---|---|---|---|---|
| 4,249,463 A | * | 2/1981 | Hornby | 454/57 |
| 4,267,769 A | * | 5/1981 | Davis et al. | 55/385.2 |
| 4,726,824 A | * | 2/1988 | Staten | 55/385.2 |
| 4,838,150 A | * | 6/1989 | Suzuki et al. | 55/385.2 |
| 4,927,438 A | * | 5/1990 | Mears et al. | 55/385.2 |
| 5,316,560 A | * | 5/1994 | Krone-Schmidt et al. | 55/385.2 |
| 5,326,316 A | * | 7/1994 | Hashimoto et al. | 55/385.2 |
| 5,342,645 A | * | 8/1994 | Eisele et al. | 427/1 |
| 5,616,171 A | * | 4/1997 | Barris et al. | 95/280 |
| 5,711,705 A | * | 1/1998 | Krainiak et al. | 55/385.2 |
| 5,858,041 A | * | 1/1999 | Luetkemeyer | 55/385.2 |
| 6,432,204 B1 | * | 8/2002 | Ueda | 55/385.2 |

* cited by examiner

Primary Examiner—Blaine Copenheaver
Assistant Examiner—Minh-Chau T. Pham
(74) Attorney, Agent, or Firm—R. Neil Sudol; Henry D. Coleman; William J. Sapone

(57) ABSTRACT

A fingerprint capture or processing apparatus incorporates a casing defining a sealable chamber, a first support in the chamber for holding a source of a chemical fingerprint fixative agent, a second support in the chamber for holding an article to be tested for fingerprints, a filtration system connected to the chamber for removing contaminants from air in the chamber, and an air circulation assembly operatively connected to the casing for circulating air from the chamber and through the filtration system. Preferably, the air circulation assembly is a closed system, ensuring that no contaminants will be spilled to the ambient atmosphere prior to complete cleansing of the air inside the casing. A humidity control device may be connected to the air circulation assembly for modifying a humidity level in the chamber to a predetermined relative humidity, thus optimizing effectiveness of the chemical fingerprint fixation agent.

20 Claims, 3 Drawing Sheets

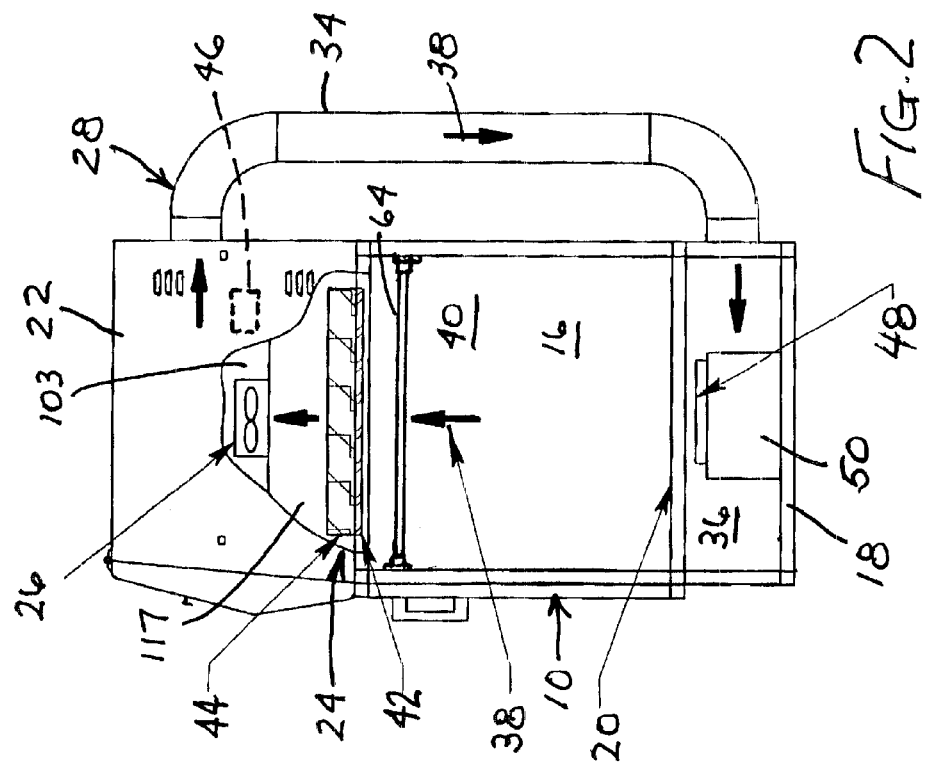
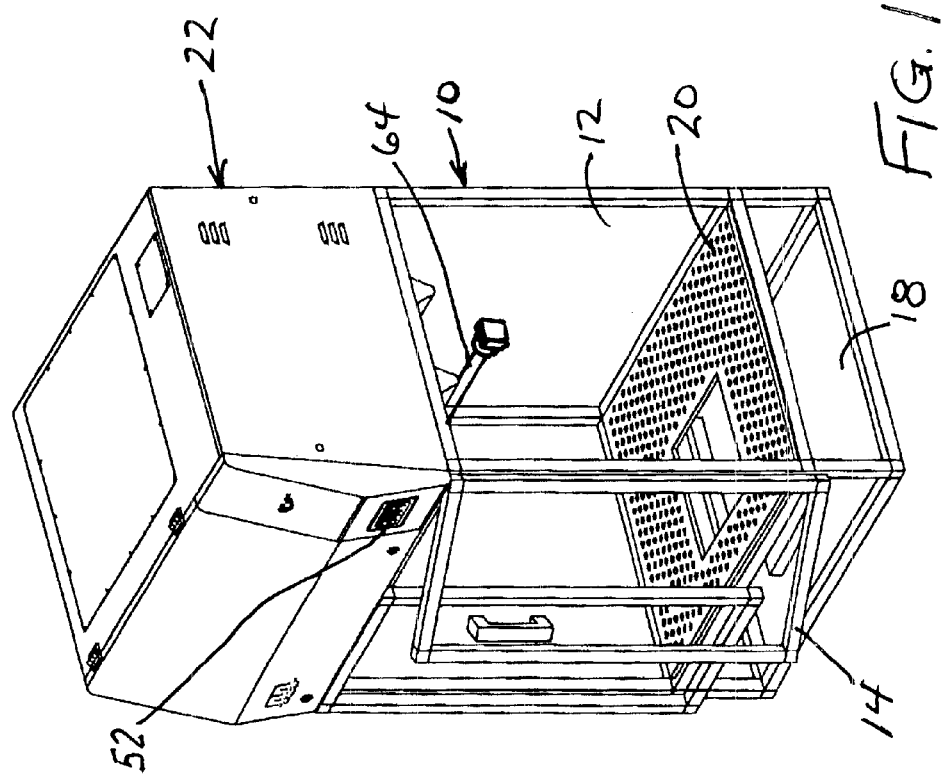

FINGERPRINT PROCESSING CHAMBER WITH AIRBORNE CONTAMINANT CONTAINMENT AND ADSORPTION

CROSS-REFERENCE TO RELATED APPLICATION

This application claims the benefit of U.S. Provisional Patent Application No. 60/231,638 filed Sep. 11, 2000.

BACKGROUND OF THE INVENTION

This invention relates to fingerprint processing. More particularly, this invention relates to the capture of fingerprints from generally inanimate objects. The invention is particularly useful in the science of forensics.

For the past 100 years, law enforcement agencies have collected human fingerprints from crime scenes in order to identify the perpetrators of various felonious crimes from petty larcenies to murders. In the past, the fingerprints were discovered at the scene and crime scene technicians would apply powders to the prints, which are actually human skin oils that are deposited on the evidence. The skin oils would adsorb the powder and become whitish in color, which allowed for either photography or removal from the evidence with adhesive tape. From the crime scene, the latent prints would be taken to a lab, photographed, categorized, and then compared visually by skilled technicians to vast quantities of prints on file. This procedure was followed in order to locate a match, thereby identifying a suspect.

Modern forensic science has improved upon this process immensely. Fingerprint identification is done now by using sophisticated computer programs run by main frame computers in such centers as the FBI fingerprint labs in Washington D.C. Manual inspection of card files is almost a thing of the past. The computers use scanning technology to read fingerprint evidence from prepared samples and automatically categorize and match the prints to corresponding prints stored in a database.

One problem that needed to be overcome to enable the law enforcement agencies to implement this system was that the latent fingerprint itself is a very fragile object. A powdered fingerprint could be easily smeared which could render it useless for comparison to known prints. Also, fingerprints are generally very faint, which led to many prints not being found in the first place. Even with the adhesive tape method, fingerprint removal from the crime scene to the lab was tenuous at best. A method was needed to enable the forensic technicians to find all fingerprints, improve the contrast between the prints and the surrounding surfaces, harden the prints so that smearing is less likely and transport from site to site is possible.

The answer was found to be a development process using fuming cyanoacrylate ester. Cyanoacrylate ester is a cyanide compound that has superior adhesive properties, especially for human tissue. It is commonly sold under trade names such as SuperGlue. As most people know, when cyanoacrylate ester is applied to two skin surfaces which are then brought into contact, the skin surfaces fuses and stick together. The result can range from merely annoying, if two fingers are fused, to extremely dangerous, if an eye membrane and skin are involved. The adhesive property of cyanoacrylate esters is so well known that medical researchers are investigating the possibility of using the compound to replace sutures in closing of wounds and incisions during operations.

Forensic scientists used this property of fusing and hardening skin oils to their advantage by heating the liquid cyanoacrylate ester and causing a mist or vapor to be formed. This vapor deposits on the latent fingerprint oils, hardens them and turns them whitish in color. When dry, the print treated by vaporous cyanoacrylate ester is very resistant to smearing, fixed to the substrate and is easily seen against a darker background. In addition. if the entire piece of evidence, such as a plastic garbage bag, gun or knife is subjected to the fumes, all fingerprints which are on the evidence will be developed and will stand out visually, reducing the possibility of losing fingerprint evidence. After developing, fingerprint evidence is processed further, allowing scanning into a computer for comparison and identification, all by techniques that are now well-known to the art.

This method has been utilized for many years with excellent results and is now the state of the art for fingerprint processing. However, some detriments are also inherent in this method.

When the cyanoacrylate ester is heated, a white vapor or mist is formed. The particle size of the vapor is very small and is easily respirable. When inhaled, the small particles can migrate into the small pulmonary channels of the lungs and cause irritation or other lung reactions that are deleterious to lung tissue. As importantly, when cyanoacrylate ester is heated, the possibility of compound breakdown exists wherein hydrogen cyanide is formed and is present in the vapor. It is well known to health experts that hydrogen cyanide (HCN) is toxic and dangerous to human health. Inhaling this compound is to be avoided.

Products have been developed to contain the vapors of cyanoacrylate ester and offer some degree of protection for the user. Generally, the design of these items is similar to laboratory fume hoods or glove boxes, wherein the evidence is placed, the sash or door closed, the liquid cyanoacrylate ester is fumed, misted, or vaporized and the fingerprints are processed. At the end of the deposition phase, the fumes are vented via a fan to an outside exhaust. By definition, this type of chamber is fixed in location, usually in a laboratory environment. Since solid connection to the ductwork is required, portability within the lab or from the lab is not possible. Also, all of the vapors are expelled to the atmosphere, increasing pollution levels emitted in the lab exhaust. If higher levels of HCN are present, a potential safety hazard is incurred since the HCN is traveling throughout the lab's ductwork.

If the process is being carried out in the field, a portable enclosure, in some cases an inverted fish tank is used to contain the vapors. At the end of the fuming cycle, the chamber is simply lifted off and the vapors are allowed to dissipate in the atmosphere. Of course, a breeze or wind could blow the vapors back into the face of the technician or deposit the vapors on other surfaces such as car paint or such.

All of these solutions, however expedient, are not fully safe, nor are they automated in any way. Technician training and experience is very critical to the fuming process, in that too much or to little cyanoacrylate ester fumes or processing time could destroy the fingerprints and therefore important case evidence. This user dependence is compounded by the realization that the fuming process is also temperature and humidity dependent, in that it is well known that best results are obtained at about 80% RH at 72 F. Control (or at least measurement) of these parameters would allow for more consistent processing.

OBJECTS OF THE INVENTION

An object of the present invention is to provide an improved apparatus and/or method for capturing a fingerprint from an object.

A more particular object of the present invention is to provide such an apparatus and/or method which is portable.

Another particular object of the present invention is to provide such an apparatus and/or method which has enhanced safety features.

An additional object of the present invention is to provide such an apparatus or method which facilitates optimal deployment of a chemical fingerprint fixative agent such as cyanoacrylate ester.

A further object of the present invention is to provide such an apparatus or method which is easy to use owing in part to automatic operation.

These and other objects of the present invention will be apparent from the drawings and descriptions herein.

SUMMARY OF THE INVENTION

An embodiment of a fingerprint capture or processing apparatus comprises, in accordance with the present invention, a casing defining a sealable chamber, a first support in said chamber for holding a source of a chemical fingerprint fixative agent, a second support in said chamber for holding an article to be tested for fingerprints, a filtration system connected to said chamber for removing contaminants from air in said chamber, and an air circulation assembly operatively connected to said casing for circulating air from said chamber and through said filtration system.

In accordance with another feature of the present invention, the fingerprint capture or processing apparatus further comprises a humidity control device connected to the air circulation assembly for modifying a humidity level in the chamber to a predetermined relative humidity. It is contemplated that the humidity control includes a humidity sensor or measurement device disposed in operative communication with the processing chamber. The humidity modification may be effectuated in part by an ultrasonic humidifier device.

In accordance with an additional feature of the present invention, the air circulation assembly includes ductwork defining a first path for directing air from the chamber through the filtration system and ductwork defining a second path bypassing the filtration system for guiding air from the chamber. The second pathway is used, for example, to circulate air through the processing chamber during a humidity adjustment process prior to a delivery of a chemical fixative agent to the processing chamber. The air circulation assembly may include a first fan or blower for moving air along the first path and a second fan or blower for moving air along the second path.

Pursuant to a further feature of the present invention, the air circulation assembly communicates with the fingerprint processing chamber near an upper end and a lower end thereof, whereby air from the chamber may be filtered or cleaned by the filtration system and subsequently returned to the chamber.

A perforated plate may be suspended from sidewalls of the casing over the first support, thereby dividing the chamber into an upper compartment and a lower compartment. In that case, the air circulation assembly is connected to the casing at the lower compartment for blowing cleaned air into the lower compartment.

Where the casing includes a door for enabling access to the chamber, the fingerprint capture or processing apparatus further comprises a contaminant sensor in operative communication with the chamber for monitoring quality of air in the chamber, and a lock mounted at least indirectly to the casing for locking the door. The lock is operatively connected to the contaminant sensor for enabling opening of the door only when the chamber is effectively void of contaminant particles.

A heating element is disposed in the fingerprint processing chamber for heating the fingerprint fixative agent during a beginning phase of a fingerprint detection procedure.

In accordance with additional features of the present invention, at least one timer is operatively connected to the air circulation assembly for determining air purge and recycle periods, while the casing includes at least one transparent panel, whereby an operator can monitor an extent of fingerprint fixation.

A method for processing objects for fingerprints comprises, in accordance with the present invention, placing an article to be tested for fingerprints into a chamber, thereafter sealing the chamber, introducing a chemical fingerprint fixative agent into the sealed chamber, cleansing or filtering air in the chamber to remove particles of the chemical fingerprint fixative agent after fixing of fingerprints on the article by the chemical fingerprint fixative agent, preventing access to the chamber after the sealing thereof and prior to the removal of the particles of the chemical fingerprint fixative agent from the chamber, and enabling access to the chamber by an operator only after cleansing or filtering of air in the chamber to effectively remove particles of the chemical fingerprint fixative agent.

A method in accordance with the present invention facilitates fingerprint capture while simultaneously protecting personnel from biologically dangerous or deleterious chemicals used in the fingerprint fixation process. The chemicals are filtered from the air of the chamber prior to the opening of the chamber after a fingerprint capture process. Access to the chamber is prevented during the fingerprint capture or fixation process, prior to removal of effectively all particles of the chemical fingerprint fixation agent.

Where the placing of the article into the chamber includes opening a door to the chamber, the article is inserted through the opened door into the chamber, and the door is subsequently closed, while the sealing of the chamber includes locking the door to prevent an opening of the door prior to the cleansing or filtering of air in the chamber.

The cleansing or filtering of air in the chamber includes circulating air from the chamber through a filtration system. Preferably, the cleansing or filtering of air in the chamber further includes returning air to the chamber after the circulating of the air through the filtration system.

A fingerprint capture apparatus and method in accordance with the present invention facilitates the capture of fingerprints by a forensic scientist or technician in part by providing easy access to the processing chamber (where the access door is a front panel of the casing) and in part by providing safety features which protect the user from the cyanoacrylate ester vapors. In addition, a fingerprint capture apparatus and method in accordance with the present invention enables the measuring and/or control of internal temperature and humidity, thereby optimizing the generation and application of cyanoacrylate ester vapors. A fingerprint capture apparatus and method in accordance with the present invention is easily portable within or from a lab and ensures removal of all contaminants from the fingerprint capture or processing chamber before venting of the air from that chamber to the lab or atmosphere. Moreover, a fingerprint capture apparatus and method in accordance with the present invention may incorporate control logic to adjust and control the length of time of purge cycles, fuming cycles and cyanoacrylate ester vaporizer heater elements.

BRIEF DESCRIPTION OF THE DRAWINGS

FIG. 1 is a perspective view of a fingerprint capture or processing apparatus in accordance with the present invention.

FIG. 2 is a schematic internal view of the fingerprint capture or processing apparatus of FIG. 1, showing selected functional components and an air circulation path.

In the drawings, the same reference numerals are used to designate similar structural elements, even though there may be differences in form between different embodiments. A slight modification of the form of a structural element is not believed to substantially affect the function of that element.

DESCRIPTION OF THE PREFERRED EMBODIMENTS

Figure 3:
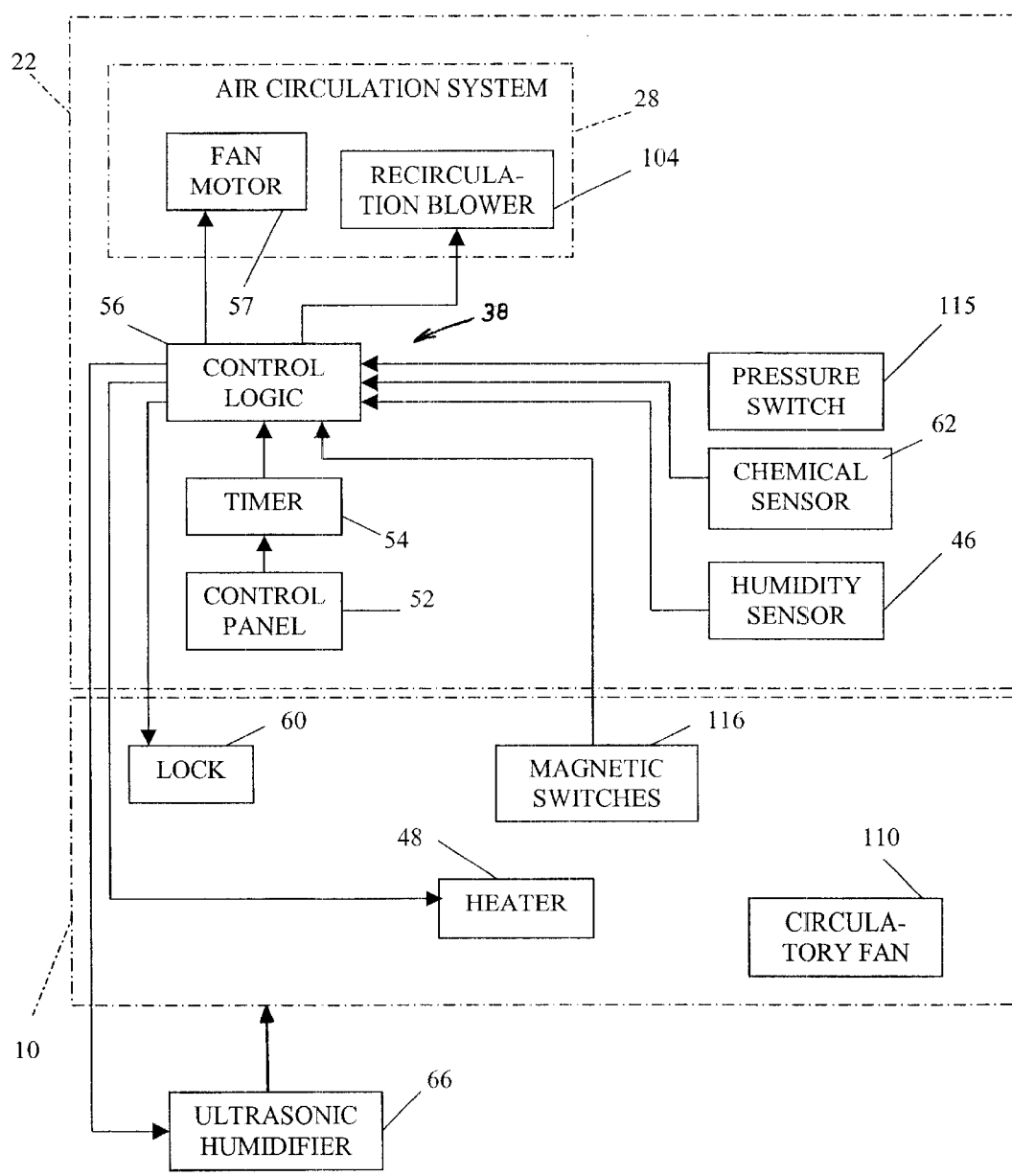
FIG. 3 is a block diagram, showing functional components of the apparatus of FIG.

As illustrated in FIGS. 1 and 2, a fingerprint capture apparatus includes a casing 10 having transparent side walls 12 and one or more lockable access doors 14 together defining a sealable processing chamber 16. Side walls 12 are solid or semi-solid panels which are preferably transparent but can alternatively be opaque or translucent. Each door 14 is preferably hinged to a side wall 12 of casing 10. However, doors 14 may take the form of any obstruction capable of being opened to allow access to processing chamber 16 and capable of being sealingly closed to prevent the escape of chemical fumes.

Casing 10 includes a solid bottom or base panel 18 fastened to side walls 12. All seams created by the four bottom edges of side walls 12 and the contiguous outer edges of base panel 18 are sealed gas tight. A second base or horizontal support 20 is suspended from side walls 12 above the level of the bottom or base panel 18 by standoffs or hangers 20 of any type. Base panel or support 20 is perforated to allow airflow through it with minimal restriction. Base panel or support 20 is spaced above bottom or base panel 18 by a predetermined but variable distance. Although a cubic enclosure or processing chamber 16 is illustrated, any geometric shape (as well as size) may be employed without straying from the intent of the instant disclosure.

The fingerprint capture apparatus of FIGS. 1 and 2 further includes a housing structure 22 disposed above casing 10 for enclosing a filtration system 24, an air circulation fan or blower 26 of an air circulation assembly 28, air circulation duct work 30 and control electronics 32 (see FIG. 3). The top edges of side walls 12 are sealed air tight against the lower side of housing structure 22. It is within the level of skill in the art to attach housing structure 22 to casing 10 so that the casing may be easily removable from the housing structure, with the side walls 12 hinged to the bottom of the housing structure. In this manner, the fingerprint capture or processing apparatus may be taken apart and folded down for easy storage or transportability.

Figure 4:
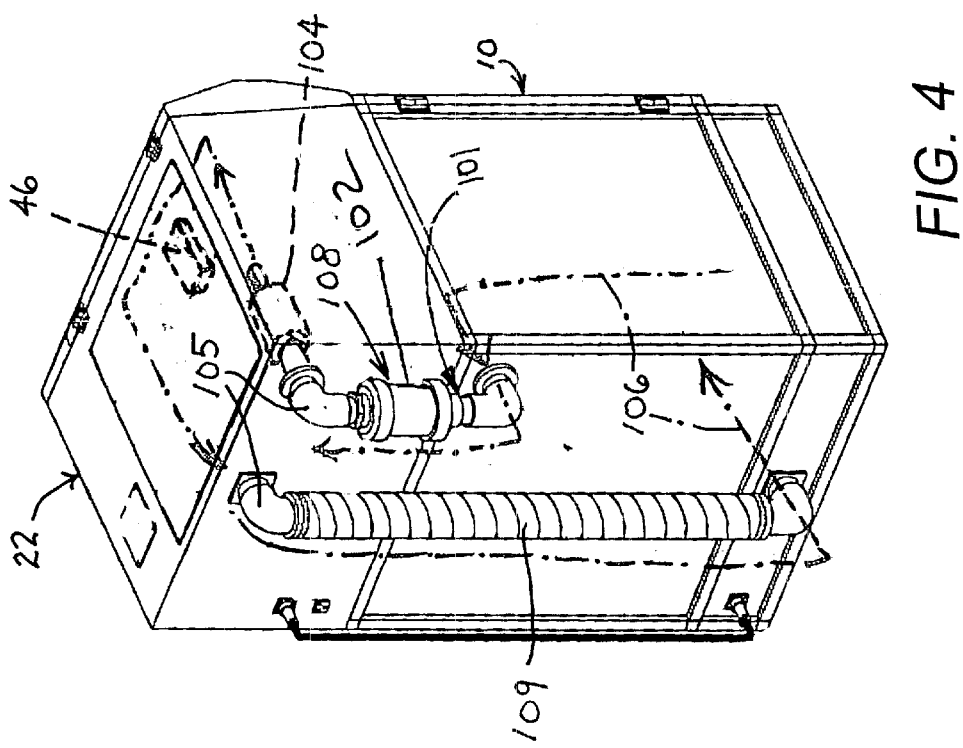
FIG. 4 is a front, top and right side perspective view of a modified fingerprint capture or processing apparatus in accordance with the present invention.

As illustrated in FIG. 4, a source of atomized water particles 66 such as an ultrasonic humidifier may be attached to one of the side walls 12 of casing 10 via a duct 111 and a flange 112. A circulatory fan 110 is disposed between the horizontal support 20 and base panel 18. A line 113 drawn perpendicular to base panel 18 and colinear with the fan's central axis is preferably co-planar with an axis 114 of connecting flange 112.

Air circulation assembly 28 does not exhaust directly to the ambient atmosphere, exterior to casing 10 and housing structure 22. Instead, air circulation assembly 28 includes a duct 34 of any shape attached to housing structure 22 and casing 10 so as to allow the cabinet air to be returned to a base or lower compartment 36 (below base panel or horizontal support 20) after removal of all toxic and noxious compounds by air filtration system 24 so that when a front door or portal 14 is opened, only cleaned air can escape. Fan or blower 26 provides sufficient motive energy to move the air through the apparatus by means known to the art. Air return duct 34 is attached to casing 10 at the lower compartment 36 via a flange arrangement disposed between the bottom or sealing base panel 18 of casing 10 and the suspended horizontal support 20. In this manner, the air can be circulated along the path indicated by arrows 38, from the lower compartment 36 of casing 10, through an upper compartment 40 of processing chamber 16, through filtration system 24, and back to base or lower compartment 36 again.

Air filtration system 24 comprises a fibrous prefilter 42, which is sized to remove small particles by means of mechanical constriction or electrostatic attraction. These filters are commonly available through industrial supply sources. In addition, air filtration system 24 comprises activated carbon filter media 44. In practice, air filtration system 24 may be a combination of a layer of standard activated carbon granules and a layer of carbon impregnated with chemicals which will adsorb and react with cyanide compounds. In this manner, one filter assembly may remove cyanoacrylate ester, odors and cyanide from the air. Alternatively, two (or more) separate filters may be employed. Of course, the filters must be installed and sealed using techniques known to the art so that air cannot bypass the filters.

As illustrated in FIG. 3, control electronics 32 includes a humidity or moisture sensor 46 located inside plenum 103, set to monitor the relative humidity levels inside processing chamber 16 and to provide an analog output proportional with the relative humidity values. The humidity sensor 46 is exposed to the relative humidity levels inside processing chamber 16 due to its location along air path 106. In order to ensure that the relative humidity levels along path 106 are of close or equal values, circulatory fan 110 is operated in conjunction with humidifier 66. More particularly, humidity sensor 46 is part of a humidity control (not separately designated) for ensuring that the humidity level in processing chamber 16 at the onset of a fingerprint capture operation is at a preselected relative humidity optimal for the generation of gaseous vapor from a liquid chemical fingerprint fixation agent (e.g., cyanoacrylate ester) deposited (in a tray) on a hot plate 48 in turn disposed in a support 50 in lower compartment 36 of processing chamber 16.

As further illustrated in FIG. 3, control electronics 32 includes an input or control panel 52 such as a keypad for setting a length of time for fuming cycles and air purge cycles. Control electronics 32 additionally includes a timer 54 for measuring out preset cycle periods. Air circulation assembly 28 operates for the preset periods to move air from processing chamber 16 through air filtration system 24 to remove chemical particles (e.g., cyanoacrylate ester and hydrogen cyanide) from the chamber air. Control electronics 32 further includes magnetic switches 116 for confirming a closed position for doors 14 and 107. Control electronics 32 also includes a pressure switch 115 to monitor the pressure drop level across fan or blower 26. This ensures that filter 24 is set so it cannot be bypassed by air moving along air path 38.

Input or control panel 52 is operatively connected to a control logic module 56 (optionally located in the housing structure 22) containing logic type controls or microprocessors which control the operation of the automatically functioning components illustrated in FIG. 3. In particular, control logic module 56 is operatively connected to a motor 57 of fan or blower 26, to humidity measurement sensor 46, and to an automatic door lock 60. Lock 60 is operatively connected to portal or door 14 for preventing access to processing chamber 16 after a sealing of door 14 and prior to an effectively complete removal, from the chamber, of particles of the chemical fingerprint fixative agent heated by hot plate or heater 48. Control logic module 56 is operatively connected to lock 60 for enabling access to processing chamber 16 by an operator only after sufficient operation of air circulation assembly 28 to effectively cleanse or filter air in the chamber to remove particles of the chemical fingerprint fixative agent (e.g., cyanoacrylate ester). A chemical sensor 62 (FIG. 3) is disposed in operative communication with a plenum 117 (FIG. 2) for detecting the presence of particles of the chemical fingerprint fixation agent used. Sensor 62 is operatively connected to control logic module 56 for signaling, to that unit, breakthrough of the chemical fixation agent past the air filtration system 24, so that module 56 allows lock 60 and subsequently door 14 to be opened only after a timed operation of blower 26 and in the absence of any output signals from chemical sensor 62. This ensures that the air in chamber 16 has been cleaned to an acceptable contaminant content.

Control logic module 56 of control electronics 32 is also connected to heater or hot plate 48 for energizing the hot plate during a fingerprint capture operation initiated by operator input via control panel 52. Control logic module 56 turns the hot plate off at the completion of a timed cycle or in response to an operator triggered signal from control panel 52. The operator can terminate the session upon visually detecting the presence of fingerprints on an article inserted into processing chamber 16.

Monitoring circuits and alarms (not illustrated) may be provided for tracking filter life. Also, safety circuits and devices such as line fuses, EMC line filters, and over temperature monitors and controls.

As illustrated in FIG. 4, a fingerprint capture apparatus may include on a front side, an additional lockable door 107 which provides access to lower compartment 36. Door 107 is preferably hinged to a front panel of casing 10 and effectuates a sealed engagement therewith. Door 107 may take the form of any obstruction capable of being opened to allow access to lower compartment 35 and capable of being sealingly closed to prevent the escape of chemical fumes.

Figure 5:
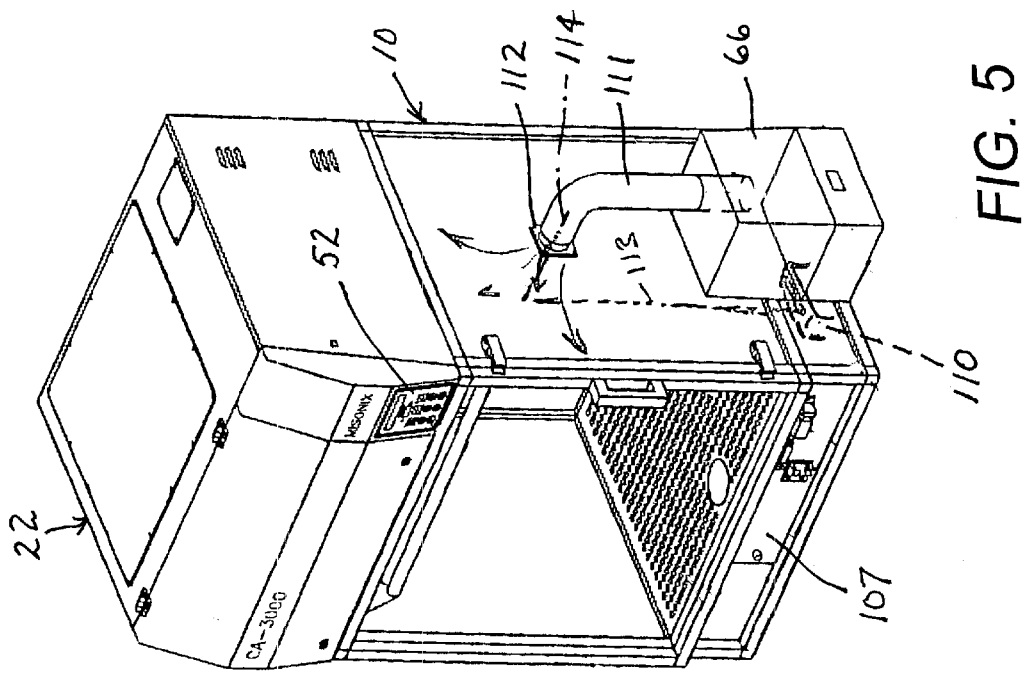
FIG. 5 is a back, top and left side perspective view of the apparatus of FIG. 4.

As depicted in FIG. 5, a fingerprint capture or processing apparatus as described herein may be provided with an ancillary air circulation system 101 which does not exhaust directly to the ambient atmosphere. Instead, air circulation system 101 includes a one-way valve 102 attached to housing structure 22 and casing 10 so as to allow the cabinet air to be moved from casing 10 into a plenum 103 above the air filtration system 24 and blower 26, and then back to the base or lower compartment 36 (below base panel or horizontal support 20). Airflow generated by a fan or blower 104 ensures that filtration system 24 is bypassed while the air circulation system 101 is used. Fan or blower 104 provides sufficient motive energy to move air through the apparatus by means known to the art. Air return or air-flow guide ducts 108 and 109 are attached to casing 10 and housing structure 22 via flange-elbows 105. In this manner, air can be circulated along a path indicated by arrows 106, from the lower compartment 36 of casing 10, through upper compartment 40 of processing chamber 16, along guide duct 108, through plenum 103, along duct 109, and back to base or lower compartment 36 again. It is to be noted that air return duct 109 (FIG. 5) may be the same as air return-duct 34 (FIG. 2), so that in both air circulation assembly 28 and air circulation system 101, air is returned to the lower compartment 36 of processing chamber 16 by a single duct.

The apparatus of FIGS. 1–5 is generally used in a fingerprint capture process as follows:

The apparatus is connected to a specified power source, such as a 115VAC 60 Hz electric socket. A main power switch (e.g., on control panel 52) is turned on. Control electronics 32 and particularly control logic 56 generally executes a start routine which allows the stabilization of circuits and the monitoring of filter conditions and ambient air conditions. A ready message (e.g., on control panel 52) signifies that the apparatus is in a condition for process commencement. The user will place an article of forensic evidence into chamber 16 by either suspending the article from an internal hanger rod 64 or on a stand (not shown) disposed on horizontal support 20. Generally, the article of evidence will be arranged such that all surfaces of the article will be exposed to the vapors of the chemical fingerprint fixation agent (e.g., cyanoacrylate ester), as opposed to laying the article on support 20. In addition, the user will place an aluminum tray (not shown) containing a small amount of liquid cyanoacrylate ester on the exposed hot plate 48 which is initially cool. At this juncture doors 14 and 107 are closed and secured.

The user engages the system by pressing a Start Cycle button (not shown) on control panel 52. The door lock 60 is normally closed and in locked condition. Control logic module 56 then activates recirculatory blower 104 and circulating fan 110 in order to establish current ambient conditions. Sensor 46 measures the relative humidity of the air in processing chamber 16 and communicates the measurement to control logic module 56. Module 56 then adjusts the humidity in chamber 16 to a relative humidity level (preset, for example, via control panel 52) by engaging and disengaging an ultrasonic humidifier 66, recirculatory blower 104 and circulating fan 110. If for some reason the humidity level is not reached, an alarm will sound and the system will abort, preventing damage to the evidence.

After the preset humidity level is reached, as measured by sensor 46, control logic module 56 disengages recirculatory blower 104, circulatory fan 110 and humidifier 66. At that time, control logic module 56 will energize hot plate 48 to preset levels and actuate circulatory fan 110. Circulatory fan 110 ensures homogenous conditions within the processing chamber 16. At about 80 to 90 degrees C., the cyanoacrylate ester will begin to vaporize. This vaporization will continue as a user set timed cycle and under user observation. Additional cyanoacrylate ester could be added as needed via the hot plate access door 107. This ensures the continuation of an already initiated cycle while minimizing the operator's exposure to the cyanoacrylate fumes. The open condition of door 107 is picked up via the magnetic switch 116. As a result an audio-visual alarm is triggered. If the technician feels that the fingerprints have reached proper stage of development prior to the completion of the timed cycle, then he or she will press a Purge Cycle switch (not separately shown) on control panel 52. This action will allow the control logic 66 to turn off power to hot plate 48, engage air fan or blower 26 and begin the measurement of a purge cycle by timer 54. During this period, the air in the processing chamber 16 will be recycled through filtration system 24 to cleanse the air of the vapors and chemicals. A purge cycle will be triggered automatically if the magnetic switch 116 senses an open condition of access door 14. Sensor 62 monitors the chemical content of the filtered air and provides an analog output to the control logic 56. An analog signal greater than a preset threshold indicates that chemicals are still present in the gas stream after purging and triggers an alarm (not illustrated).

Hot plate 48 cools down and the vapor emissions will cease. After a preset period, the air fan or blower 26 will disengage, and the door lock 60 can be disengaged by pressing the Unlock button (not shown) located on control panel 52. A Purge Cycle Complete message will be displayed on control panel 52. The user may then open the door 14 and remove the evidence. At this point, another tray of cyanoacrylate ester may be prepared and the sequence started again with another piece of evidence. When all of the devices, controls and apparatus are assembled in the manner described herein, a safe, secure and automated fingerprint development system can be constructed and utilized.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A fingerprint processing apparatus comprising:
   a casing defining a sealable chamber;
   a first support in said chamber for holding a source of a chemical fingerprint fixative agent;
   a second support in said chamber for holding an article to be tested for fingerprints;
   a filtration system connected to said chamber for removing contaminants from air in said chamber; and
   an air circulation assembly operatively connected to said casing for circulating air from said chamber and through said filtration system.

2. The processing apparatus defined in claim 1, further comprising a humidity control device connected to said air circulation assembly for modifying a humidity level in said chamber.

3. The processing apparatus defined in claim 2 wherein said air circulation assembly includes ductwork defining a first path for directing air from said chamber through said filtration system and ductwork defining a second path bypassing said filtration system for guiding air from said chamber.

4. The processing apparatus defined in claim 3 wherein said air circulation assembly includes a first fan or blower for moving air along said first path and a second fan or blower for moving air along said second path.

5. The processing apparatus defined in claim 2 wherein said humidity control includes a humidity sensor or measurement device.

6. The processing apparatus defined in claim 1 wherein said air circulation assembly communicates with said chamber near an upper end and a lower end thereof, whereby air from said chamber may be filtered or cleaned by said filtration system and subsequently returned to said chamber.

7. The processing apparatus defined in claim 4 wherein said, further comprising a perforated plate suspended from sidewalls of said casing over said first support, thereby dividing said chamber into an upper compartment and a lower compartment, said air circulation assembly being connected to said casing at said lower compartment and said upper compartment.

8. The processing apparatus defined in claim 1 wherein said fingerprint fixative agent is cyanoacrylate ester.

9. The processing apparatus defined in claim 1, further comprising a heating element disposed in said chamber for heating said fingerprint fixative agent during a beginning phase of a fingerprint detection procedure.

10. The processing apparatus defined in claim 1, further comprising at least one timer operatively connected to said air circulation assembly for determining air purge and recycle periods.

11. The processing apparatus defined in claim 1 wherein said casing includes at least one transparent panel, whereby an operator can monitor an extent of fingerprint fixation.

12. The processing apparatus defined in claim 1 wherein said second support includes a perforated plate suspended from sidewalls of said casing over said first support.

13. The processing apparatus defined in claim 1 wherein said filtration system includes a fibrous prefilter and activated carbon filter media.

14. A method for processing objects for fingerprints, comprising:
    placing an article to be tested for fingerprints into a chamber;
    thereafter sealing said chamber;
    after the sealing of said chamber, introducing a chemical fingerprint fixative agent into said chamber while maintaining said chamber in a sealed condition;
    after fixing of fingerprints on said article by said chemical fingerprint fixative agent, cleansing or filtering air in said chamber to remove particles of said chemical fingerprint fixative agent;
    preventing access to said chamber after the sealing of said chamber and prior to the removal of the particles of said chemical fingerprint fixative agent from said chamber; and
    enabling access to said chamber by an operator only after cleansing or filtering of air in said chamber to effectively remove particles of said chemical fingerprint fixative agent.

15. The method defined in claim 14 wherein the placing of said article into said chamber includes opening a door to said chamber, inserting the article through the opened door into said chamber and subsequently closing said door, the sealing of said chamber including locking said door to prevent an opening of said door prior to the cleansing or filtering of air in said chamber to effectively remove particles of said chemical fingerprint fixative agent.

16. The method defined in claim 14, wherein the introducing of said chemical fingerprint fixative agent into said chamber includes heating a deposit of said chemical fingerprint fixative agent in said chamber to disperse particles of said chemical fingerprint fixative agent into air in said chamber.

17. The method defined in claim 14 wherein the cleansing or filtering of air in said chamber includes circulating air from said chamber through a filtration system.

18. The method defined in claim 14 wherein the cleansing or filtering of air in said chamber further includes returning air to said chamber after the circulating of the air through said filtration system.

19. The method defined in claim 14, further comprising automatically modifying a humidity level in said chamber, after sealing said chamber, so that air in said chamber attains a selected relative humidity prior to introduction of said chemical fingerprint fixative agent into said chamber.

20. A fingerprint processing apparatus comprising:
   a casing defining a sealable chamber, said casing including a door for enabling access to said chamber;
   a first support in said chamber for holding a source of a chemical fingerprint fixative agent;
   a second support in said chamber for holding an article to be tested for fingerprints;
   a filtration system connected to said chamber for removing contaminants from air in said chamber;
   an air circulation assembly operatively connected to said casing for circulating air from said chamber and through said filtration system;
   a contaminant sensor in operative communication with said chamber for monitoring quality of air in said chamber; and
   a lock mounted at least indirectly to said casing for locking said door, said lock being operatively connected to said contaminant sensor for enabling opening of said door only when said chamber is effectively void of contaminant particles.

* * * * *